(12) United States Patent  (10) Patent No.: US 6,198,969 B1
Kuzma  (45) Date of Patent: Mar. 6, 2001

(54) IMPLANTABLE CONNECTOR FOR MULTI-OUTPUT NEUROSTIMULATORS

(75) Inventor: Janusz A. Kuzma, Englewood, CO (US)

(73) Assignee: Advanced Bionics Corporation, Sylmar, CA (US)

( * ) Notice: Subject to any disclaimer, the term of this patent is extended or adjusted under 35 U.S.C. 154(b) by 0 days.

(21) Appl. No.: 09/239,926

(22) Filed: Jan. 28, 1999

Related U.S. Application Data

(60) Provisional application No. 60/074,519, filed on Feb. 12, 1998.

(51) Int. Cl.[7] ....................................... A61N 1/375
(52) U.S. Cl. .................................. 607/37; 607/38
(58) Field of Search .......................... 607/37, 38

(56) References Cited

U.S. PATENT DOCUMENTS

| | | |
|---|---|---|
| 4,142,532 | 3/1979 | Ware . |
| 4,180,078 | 12/1979 | Anderson . |
| 4,411,276 | 10/1983 | Dickhudt . |
| 4,411,277 | 10/1983 | Dickhudt . |
| 4,516,820 | 5/1985 | Kuzma . |
| 5,070,605 | 12/1991 | Daglow et al. . |
| 5,336,246 * | 8/1994 | Dantanarayana . |
| 5,755,743 * | 5/1998 | Volz et al. ............... 607/37 |
| 6,006,135 * | 12/1999 | Kast et al. . |

* cited by examiner

Primary Examiner—Carl H. Layno
(74) Attorney, Agent, or Firm—Bryant R. Gold

(57) ABSTRACT

A multi-output connector for use with an implantable neurostimulator, or similar implantable stimulator, is described. The connector includes three main components: an output bracket (10), a receiver (20), and a clamp (30). The output bracket forms part of the stimulator and is typically made from a hard polymer, such as epoxy resin. It has a T-shaped cross section, and has an array of metal contacts placed on both sides of the base of the "T". The receiver is made from a soft polymer, such as silicone rubber, and has a T-slot formed therein adapted to match the T-shaped cross-section of the output bracket. Contact pins are formed in the side walls of the receiver so as to make electrical contact with the metal contacts of the output bracket when the receiver is placed over the bracket. The clamp is made from metal in the form of a U-shape and fits over the top of the receiver 20 to apply compression to both side of the receiver. The compression provided by the clamp not only assures proper electrical contact between the metal contacts of the output bracket and the corresponding pins of the receiver, but also deforms the silicone walls of the receiver to provide the necessary electrical insulation and sealing between the connection points.

13 Claims, 3 Drawing Sheets

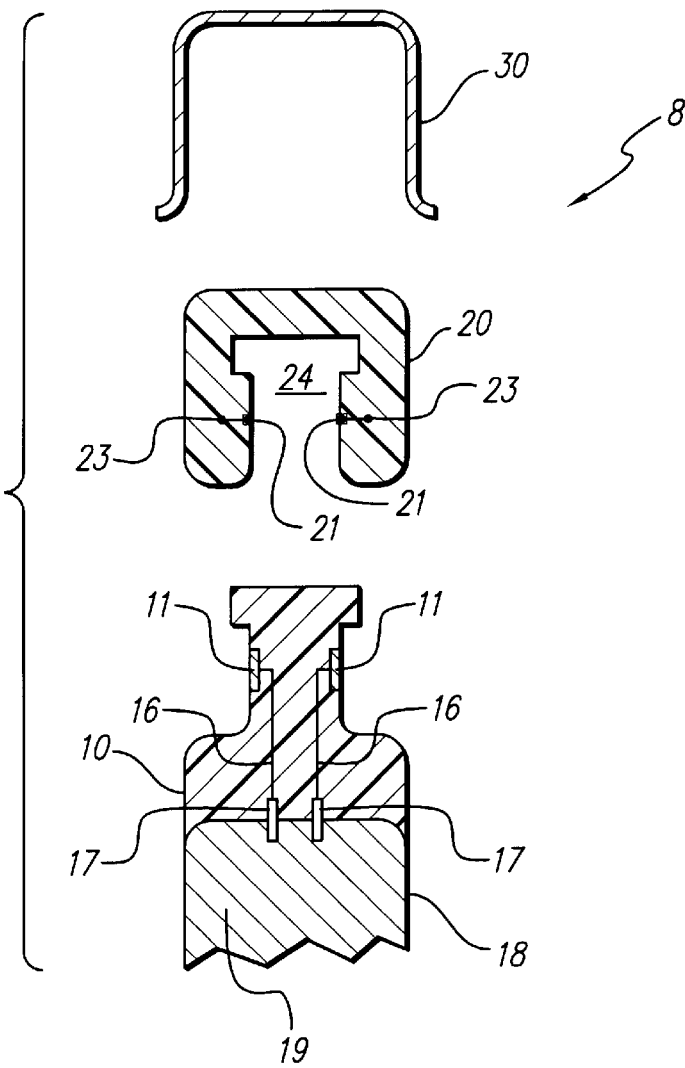
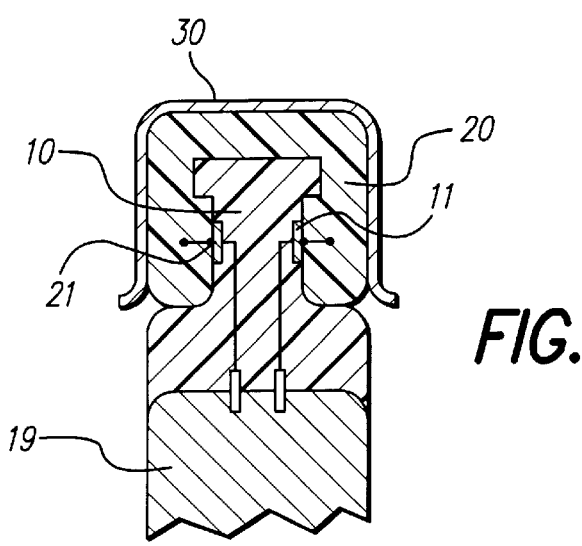

IMPLANTABLE CONNECTOR FOR MULTI-OUTPUT NEUROSTIMULATORS

This application claims the benefit of U.S. Provisional Application Ser. No. 60/074,519, filed Feb. 12, 1998.

BACKGROUND OF THE INVENTION

The present invention relates to implantable neurostimulators, and more particularly to a connector for use with a multi-output neurostimulator or similar implantable stimulator or other multi-output device.

There is a need in the art for a reliable connector that can detachably connect an electrical lead, having a multiplicity of electrical conductors therein (which electrical conductors may be connected to electrodes, sensors, or other devices or elements), to an implantable electrical device in an easy and secure manner.

Current pacemaker-type connectors, which connect the proximal end of a lead to an implantable pacemaker, which lead has a distal end having one or more electrodes which are typically inserted in or on the heart, are difficult to make and use when there is a need for more than about four connections.

Disadvantageously, most neurostimulators have more than four electrical connections that must be made with the neurostimulator device if the device is to perform its intended function. Hence, either very complex and difficult connectors must be designed, built, and used to interface with the neurostimulator; or the neurostimulator must be configured so that the lead/electrodes form an integral part thereof, thereby eliminating the connector altogether. Unfortunately, when the connector is eliminated altogether, the manufacture, assembly and test of the device becomes more difficult and complex because the stimulator and lead/electrodes must be assembled and tested as one large assembly. Even more significantly, when a connector is not used, the service and maintenance options available to the physician/patient are severely restricted.

It is thus seen that there is a need in the art for a simple, yet reliable, connector that can be used with an implantable neurostimulator, or similar implantable stimulation devices, where more than about three or four electrical connections must be made with the device.

SUMMARY OF THE INVENTION

The present invention addresses the above and other needs by providing a multi-output (i.e., more than three or four outputs) connector adapted for use with an implantable neurostimulator, or similar implantable device. The connector includes three main components: (1) an output bracket, (2) a receiver and (3) a clamp.

The output bracket forms part of the stimulator housing and is typically made from a hard polymer, such as epoxy resin. It has a T-shaped cross section, and has an array of metal contacts placed on both sides of the base of the "T". Each metal contact represents an electrical terminal to which an electrode, or other electrical component (e.g., a sensor) used with the neurostimulator, is to be connected.

The receiver is connected to a proximal end of a lead that is to be attached to the output bracket. The receiver is made from a soft polymer, such as silicone rubber, and has a T-slot or channel formed therein adapted to match the T-shaped cross-section of the output bracket. The receiver snaps or slides over the output bracket. Contact pins are formed in the side walls of the receiver so as to make electrical contact with the metal contacts of the output bracket when the receiver is placed over the bracket. Each of these contact pins is connected through a suitable wire that passes through the lead to an electrode or other electrical component located along the length of or at a distal end of the lead.

The clamp is made from metal in the form of a U-shape and fits over the top of the receiver so as to apply a compressive force to both sides of the receiver. The compression provided by the clamp not only assures proper electrical contact between the metal contacts of the output bracket and the corresponding pins of the receiver, but also deforms the flexible soft walls of the receiver to provide the necessary electrical insulation and sealing between the connection points.

Thus, the invention provides a simple (only three parts), yet reliable and easy-to-use approach for detachably securing a multiple output electrical stimulating device to an implantable lead, which lead has multiple conductors therein (which conductors respectively attach to electrodes or other devices or components at a distal end, or along the length of, the lead).

In one embodiment, the invention may be characterized as comprising a detachable connector for use with an implantable electrical stimulator having a multiplicity of output contacts. Such connector includes a hard or stiff output bracket that forms part of the case of the implantable electrical stimulator. The output bracket has a cross section of a prescribed shape, e.g., a T-shape. Metal contacts are formed on each side of the cross section, and each metal contact is electrically connected, inside of the stimulator case, to an electrical feedthrough terminal that makes contact with appropriate electrical circuitry hermetically sealed within the case of the implantable stimulator. The connector also includes a soft or compliant receiver made from silicone rubber or a similar compliant material and is adapted to slide or snap over the output bracket. The receiver includes a channel therein having the same basic cross sectional shape as that of the output bracket. Metal pins are formed in the side walls of the receiver. Each metal pin is positioned so as to electrically contact a corresponding metal contact located in the output bracket when the receiver is fitted over the output bracket. Finally, the connector includes a U-shaped clamp that fits over the receiver and provides a compression force which forces the contact pins of the receiver in secure electrical contact with the corresponding metal contacts of the output bracket, and which further deforms the compliant walls of the receiver so as to provide electrical insulation and sealing between the various contact points included within the connector. The receiver forms a proximal end of an implanted lead that is detachably connected to the implantable stimulator by way of the connector.

The invention may further be characterized as a method for detachably connecting an implantable lead to an implantable electrical stimulator. Such electrical stimulator typically has at least four terminals to which electrical connection through the implantable lead must be established. The method includes the steps of: (a) forming an output header as part of the electrical stimulator, which output header has a specified cross section shape, e.g., a "T-shape" cross section; (b) forming at least four metal contacts in a side wall of the cross section shape of the output header so that each metal contact is flush with a surface of the side wall; (c) electrically connecting each metal contact with a corresponding terminal of the electrical stimulator; (d) forming a deformable receiver having a channel therein that fits over the output header; (e) forming at least four metal pads within the channel of the receiver so that each is flush with a surface of the channel, and so that each contacts a respective one of the metal contacts formed in the side wall of the output header when the receiver is fitted over the output header; (f) electrically connecting each metal pad within the receiver with a respective wire within the implantable lead; and (g) compressing side walls of the receiver to assure a good secure electrical contact between the metal pads in the receiver and corresponding metal contacts in the output header, and to deform the receiver so that a deformed portion of the receiver side walls insulates each of the metal contact/pad connection points from adjoining metal contact/pad connection points.

BRIEF DESCRIPTION OF THE DRAWINGS

The above and other aspects, features and advantages of the present invention will be more apparent from the following more particular description thereof, presented in conjunction with the following drawings wherein:

FIG. 2 is an exploded side sectional view of the three main components of the invention;

FIG. 3 is a side sectional view of the three main components of the invention in their assembled or connected state;

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
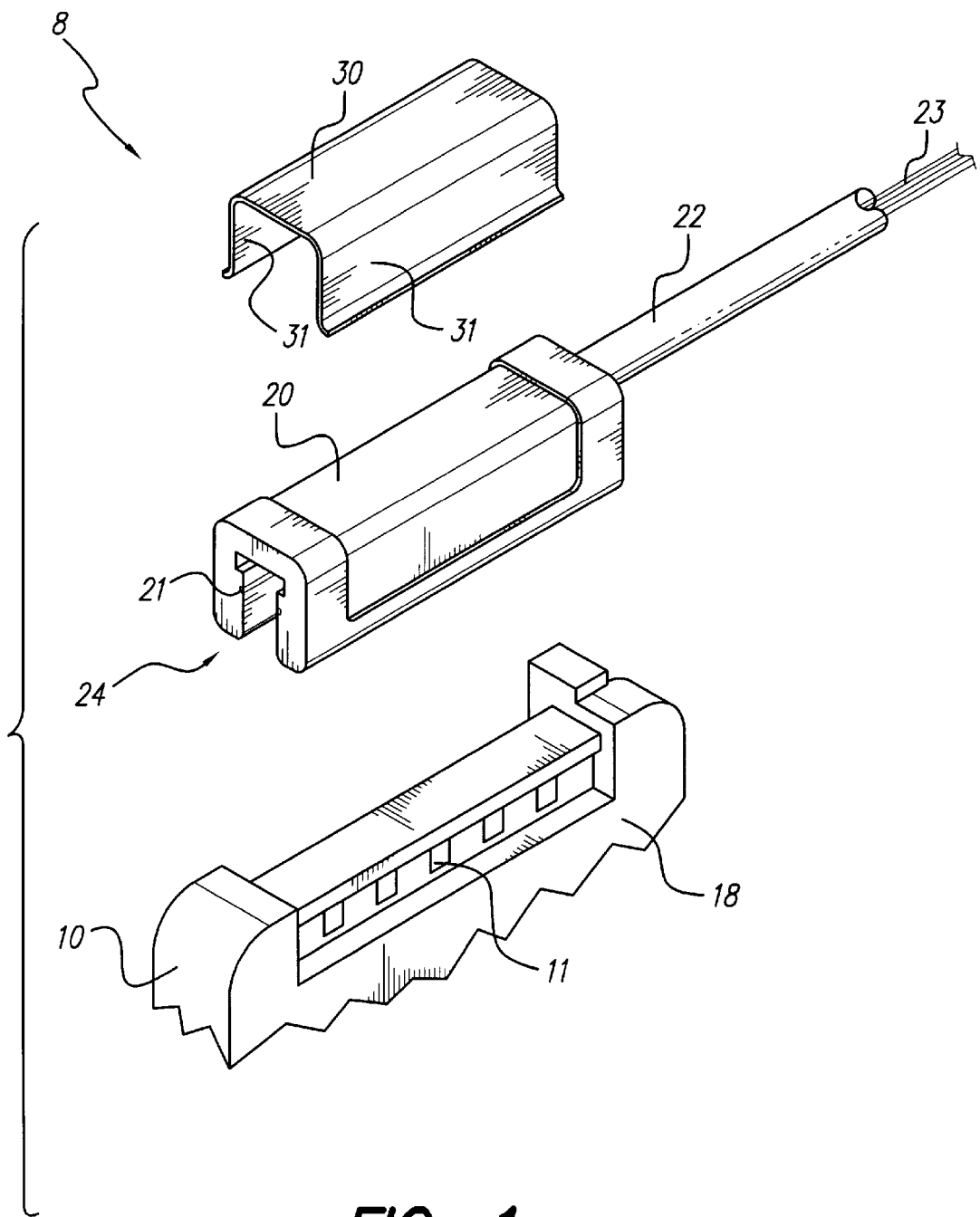
FIG. 1 is an exploded perspective view showing the three main components of the invention.

Referring first to FIGS. 1 and 2, there is shown an exploded view of the three main components a connector 8 made in accordance with the present invention. As seen in these exploded figures, the connector 8 includes an output bracket 10, a receiver 20, and a clamp 30. The output bracket 10 is part of a implantable electrical device 18. The implantable electrical device 18 may be any suitable electrical device intended for implantation, such as a neurostimulator or other tissue stimulator or sensor.

The device 18 typically includes an electrical circuit 19 hermetically sealed within a suitable sealed case in conventional manner. A battery may be included as part of the circuit 19. Electrical feedthrough pins 17 provide electrical terminals or contact points through which electrical connection must be established from a location outside of the hermetically sealed case in order for the device 18 to perform its intended function, e.g., stimulation of living tissue or nerves, or sensing of physiological signals.

As seen in FIGS. 1 and 2, the output bracket 10 is affixed to, or forms an integral part of, the implantable device 18. Preferably, the output bracket 10 is made from a hard polymer, such as epoxy resin. The bracket 10 has a cross-section of a desired shape, e.g., a "T" shape, or "bottle-top" shape, as shown best in FIG. 2. Other shapes may also be used. An array of spaced-apart metal contacts 11 are placed on both sides of a lower portion, or base, of the T-shaped cross-section (or on both sides of the neck portion of the bottle-top shape), as also seen best in FIG. 2. Each metal contact 11 is electrically connected with a respective feed-through terminal 17 by way of a wire 16 (or other conductive strip) formed within the output bracket 10. In this manner, each of the metal contacts 11 is electrically connected with the electrical circuit(s) 19 housed within the device 18.

The number of electrical contacts 11 that is used depends upon the particular type of electrical device 18 with which the connector 8 is to be used. Typically, there will be at least three such contacts 11, and more often (e.g., for neurostimulation applications) there will be many more contacts, e.g., 4–30 contacts.

The spaced-apart metal contacts 11 are formed to be flush with the surface of the side walls of the output bracket 10. Any suitable biocompatible metal, or plated metal, may be used for the metal contacts 11, e.g., platinum or its alloys, stainless steel, or the like.

The receiver 20 is typically connected at a proximal end of an implantable lead 22 (FIG. 1). At a distal end of the lead 22 (not shown), or along the length of the lead 22, there will typically be an array of electrodes, or other components (e.g., a sensor) to which the electrical circuit 19 must be electrically connected. Each electrode or other component is connected to a conductive wire 23 within the lead 22.

As seen best in FIG. 2, but also evident from FIG. 1, the receiver 20 is formed to have a channel 24 therein. The channel 24 has a cross-sectional shape that matches the cross-sectional shape of the output bracket 10. Thus, where the output bracket 10 has a T-shaped cross section, the channel 24 formed within the receiver 24 also has a T-shaped cross section, thereby allowing the receiver to fit snugly over the output bracket 10, as seen in FIG. 3.

The receiver 20 is preferably made from a suitable soft compliant material, such as silicone rubber, LSR-25, or the like, as is commonly used with implantable leads and other implantable devices.

It is the function of the connector 8 of the present invention to electrically connect the wires 23 within the lead 22 (and hence to electrically connect the electrodes or other components at the distal end or along the length of the lead 22) to the metal contacts 11 which are exposed on the side walls of the output bracket 10. That is, it is the function of the connector 8 to ultimately connect the distal electrodes/sensor(s) to the electrical circuit 19 housed within the device 18, thereby allowing the device 18 to perform its intended function. Thus, each wire 23 within the lead 22 is electrically connected to a corresponding metal pin or contact point 21 placed in the side walls of the channel 24. The metal contacts or pins 21 in the receiver 20 are positioned so as to match or "align" with corresponding metal contacts 11 of the output bracket 10 when the receiver 20 is placed over the output bracket. The contacts 21 of the receiver 20 are configured to be flush with the inside surface of the channel 24. Thus, when the receiver 20 is placed over the output bracket 10, each contact 21 within the receiver 20 aligns with and electrically contacts a respective metal contact 11 of the output bracket 10.

The connector 8 also includes a clamp 30. As seen in FIGS. 1 and 2, the clamp 30 preferably comprises a U-shape clamp, made from a suitable biocompatible springy metal, such as stainless steel, which snaps over the top of the receiver 20. The clamp is designed with sufficient spring force so as to apply the necessary compression to both sides of the receiver. Such compressive force not only serves to maintain the receiver contacts 21 in good electrical contact with the contacts 11 of the output bracket 10, but also serves to deform the walls of the receiver 20 (which receiver walls are made from silicone rubber or other suitable soft material) so as to provide necessary electrical insulation between the various connection contact pairs. That is, the compressed silicone rubber around each contact location (i.e., each location where a receiver contact 21 touches an output bracket contact 11) insulates that contact location from adjacent contact locations and from the surrounding environment.

Thus, in use, to assemble the connector 8, the receiver 20 is snapped onto the T-section (or other cross-sectional shape) of the output bracket 10. As has been explained, the T-section channel 24 of the receiver 20 fits compactly over the T-section of the output bracket 10, positioning corresponding contacts 21 and 11 together. The clamp 30 is then pushed onto the top of the receiver 20. When this occurs, the sides 31 of the clamp 30 press the sides of the receiver 20 against the wall of the output bracket 10 where the contacts 11 are located. As a result, proper electrical contact is assured between the contacts 21 and 11, and the deformation of the silicone rubber walls of the receiver 20 provides the necessary electrical insulation between the connection pairs.

Figure 4:
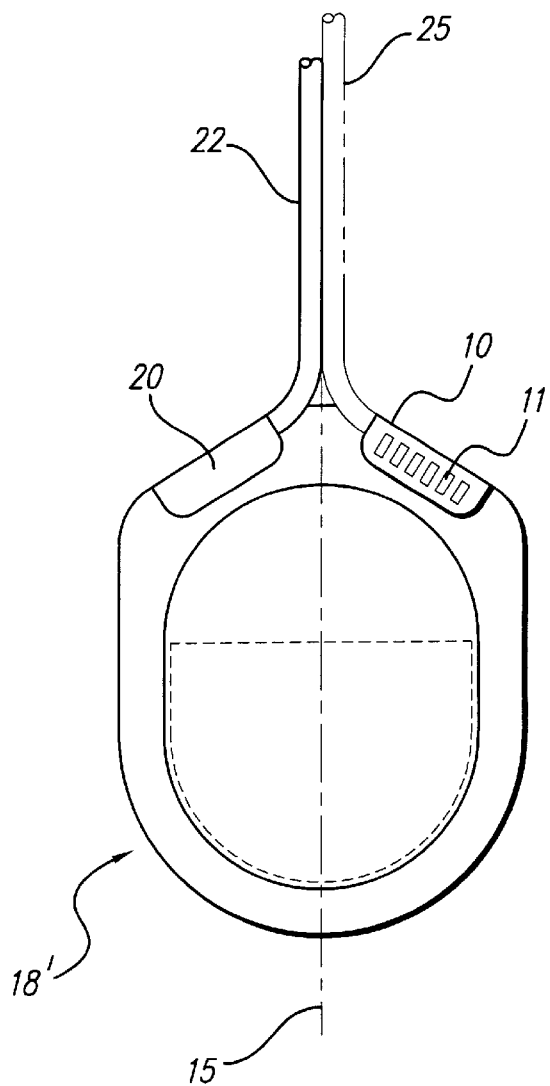
FIG. 4 is a side view of an alternate embodiment of the invention.
Figure 5:
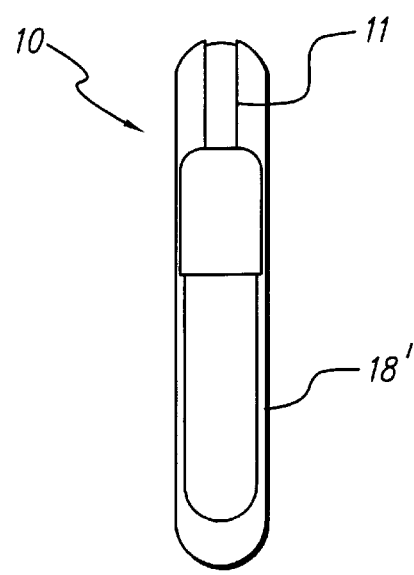
FIG. 5 is a side view of the embodiment shown in FIG. 4.

Turning next to FIGS. 4 & 5, there is shown an alternative embodiment of an implantable neurostimulator, or other implantable device, with which the connector 8 of the present invention may be used. As seen in FIG. 4, dual output blocks 10 are formed on opposite sides (left and right, as shown on FIG. 4) of an implantable device 18'. A receiver 20 is shown snapped over the left output block, while the right output block is shown without a receiver snapped thereover. Thus, a multiplicity of metal contacts 11 associated with the right output block are visible. The lead 22 associated with the left receiver 20 may be routed away from the device 18' along a center line 15. The lead associated with the right receiver, when used, may then be routed away parallel to and against the lead 22, as shown by the phantom line 25. The use of dual receivers, as shown in FIG. 4, advantageously doubles the number of outputs that may be used with the device 18'.

Advantageously, conventional materials and manufacturing processes may be used to form the output block 10, the receiver 20, and the clamp 30 which form part of the present invention.

As described above, it is thus seen that the present invention provides a detachable connector for use with an implantable electrical device, such as a neurostimulator. The detachable connector is easy to use, and it provides a secure electrical connection with multiple outputs of the electrical device. In some embodiments, multiple output blocks may be utilized, allowing the number of output terminals, or output signal lines to be significantly increased.

As further described above, it is seen that the invention provides a detachable connector for use with an implantable multichannel neurostimulator that can be readily manufactured and assembled using conventional materials and methods, and which once manufactured and assembled, provides a secure and reliable electrical connection between the various conductors of an implantable lead and electronic circuitry hermetically sealed within the neurostimulator.

While the invention herein disclosed has been described by means of specific embodiments and applications thereof, numerous modifications and variations could be made thereto by those skilled in the art without departing from the scope of the invention set forth in the claims.

What is claimed is:

1. A detachable connector for use with an implantable stimulator, the implantable stimulator having a case and a multiplicity of output contacts through which electrical connection with the implantable stimulator is made, the connector forming a proximal end of an implantable lead adapted to be detachably secured to the implantable stimulator, the implantable lead having a multiplicity of wire conductors embedded therein through which electrical contact with the implantable stimulator is to be made, said detachable connector comprising:

an output bracket that forms part of the case of an implantable electrical stimulator, the output bracket having a cross section of a prescribed shape, wherein metal contacts are formed on each side of the cross section, and wherein each metal contact is electrically connected to electrical circuitry hermetically sealed within the case;

a soft receiver made from a compliant material adapted to fit over the output bracket, the receiver having a channel therein with the same approximate cross sectional shape as that of the output bracket, the receiver including metal pins formed in side walls of the channel which are positioned to electrically contact a corresponding metal contact located in the output bracket when the receiver is fitted over the output bracket; and a U-shaped clamp adapted to fit over and compress the soft receiver against the output bracket, thereby maintaining the contact pins of the receiver in secure electrical contact with corresponding metal contacts of the output bracket, wherein the compliant walls of the receiver are deformed by the U-shaped clamp so as to provide electrical insulation and sealing between the various contact points included within the connector.

2. The detachable connector of claim 1 wherein the receiver is made from silicone rubber.

3. The detachable connector of claim 2 wherein the metal pins within the channel of the receiver are flush with the walls of the channel.

4. The detachable connector of claim 1 wherein the output bracket is made from a hard polymer.

5. The detachable connector of claim 4 wherein the hard polymer comprises epoxy resin.

6. The detachable connector of claim 3 wherein the metal contacts formed in the output bracket are formed to be flush with the surface of the output bracket.

7. A connector for detachably connecting an implantable lead with an implantable electronic device, the implantable electronic device having at least four terminals to which electrical connection through the implantable lead must be established, the connector comprising:

an output header affixed to the implantable electronic device, the output header having a first contact surface in which at least four metal contacts are formed so as to be flush with the first contact surface, each metal contact being electrically connected with a corresponding terminal of the implantable electronic device;

a deformable receiver adapted to fit over the output header, the deformable receiver having a second contact surface adapted to lie against the first contact surface of the output header when the receiver is fitted over the output header, the second contact surface having at least four metal pads formed therein so as to be flush with the second contact surface, each metal pad being positioned to contact a respective one of the metal contacts formed in the first contact surface when the receiver is fitted over the output header, and each metal pad being electrically connected with a respective wire within said implantable lead; and clamp means adapted to snap over the receiver for applying a compressive force to the receiver so as to assure a good secure electrical contact between the metal pads in the receiver and the corresponding metal contact in the output header, said compressive force further deforming the receiver whereby a deformed portion of the receiver insulates each of the metal contact/pad connection points from adjoining metal contact/pad connection points.

8. The detachable connector of claim 7 wherein said output header has a specified cross section shape, the first contact surface comprising a side wall of said cross section shape, and wherein said receiver has a channel formed therein having a cross section shape that matches the cross section shape of the output header, the second contact surface comprising a side wall of said channel.

9. The detachable connector of claim 8 wherein the specified cross section shape of the output header comprises a T-shape, and wherein the first contact surface comprises a side wall of the base of the T-shaped cross section.

10. The detachable connector of claim 9 wherein the metal contacts are formed in both side walls of the T-shaped cross section.

11. The detachable connector of claim 7 wherein the means for applying a compressive force comprises a U-shaped clamp adapted to snap over said receiver.

12. A method for detachably connecting an implantable lead to an implantable electrical stimulator, the electrical stimulator having at least four terminals to which electrical connection through the implantable lead must be established, the method comprising:

forming an output header as part of the electrical stimulator, the output header having a specified cross section shape;

forming at least four metal contacts in a side wall of the cross section shape of the output header so that each is flush with a surface of the side wall, and electrically connecting each metal contact with a corresponding terminal of the electrical stimulator;

forming a deformable receiver having a channel therein that fits over the output header;

forming at least four metal pads within the channel in the receiver so that each is flush with a surface of the channel, and so that each contacts a respective one of the metal contacts formed in the side wall of the output header when the receiver is fitted over the output header, and electrically connecting each metal pad with a respective wire within said implantable lead; and compressing the receiver to assure a good secure electrical contact between the metal pads in the receiver and the corresponding metal contact in the output header, and to deform the receiver so that a deformed portion of the receiver insulates each of the metal contact/pad connection points from adjoining metal contact/pad connection points.

13. The method of claim 12 wherein the step of compressing the receiver comprises placing a U-shaped bracket over the receiver.

* * * * *